(12) United States Patent
Brodland et al.

(10) Patent No.: US 9,134,209 B2
(45) Date of Patent: Sep. 15, 2015

(54) APPARATUS FOR INTERFACING WITH A TEST SPECIMEN

(75) Inventors: G. Wayne Brodland, Waterloo (CA); Caleb Richard Horst, Waterloo (CA)

(73) Assignee: Waterloo Instruments Inc., Waterloo (CA)

( * ) Notice: Subject to any disclaimer, the term of this patent is extended or adjusted under 35 U.S.C. 154(b) by 279 days.

(21) Appl. No.: 13/313,560

(22) Filed: Dec. 7, 2011

(65) Prior Publication Data

US 2013/0145858 A1    Jun. 13, 2013

(51) Int. Cl.
*G01N 3/08* (2006.01)
*G01N 3/04* (2006.01)

(52) U.S. Cl.
CPC .......... *G01N 3/04* (2013.01); *G01N 2203/0089* (2013.01); *G01N 2203/0435* (2013.01)

(58) Field of Classification Search
USPC .......................................................... 73/788
See application file for complete search history.

(56) References Cited

U.S. PATENT DOCUMENTS

| | | | |
|---|---|---|---|
| 4,677,854 A * | 7/1987 | Gabelli | 73/794 |
| 5,468,138 A * | 11/1995 | Bosse et al. | 425/383 |
| 6,247,370 B1 * | 6/2001 | Ramaswamy et al. | 73/857 |
| 7,051,600 B1 * | 5/2006 | Cavallaro et al. | 73/862.041 |
| 7,204,160 B1 * | 4/2007 | Sadegh et al. | 73/862.041 |
| 7,509,882 B2 * | 3/2009 | Monteiro et al. | 73/862.046 |
| 7,762,146 B2 * | 7/2010 | Brodland | 73/856 |
| 8,082,802 B1 * | 12/2011 | Sadegh et al. | 73/856 |

* cited by examiner

*Primary Examiner* — Lisa Caputo
*Assistant Examiner* — Octavia Hollington
(74) *Attorney, Agent, or Firm* — Gowling Lafleur Henderson LLP; Jeffrey W. Wong (57) ABSTRACT

The disclosure is directed at a system for applying a displacement, strain, stress or load to a test specimen. The system includes an interface manufactured from a deformable material which is connected to an actuator and to the test specimen. Application of a displacement by the actuator causes the test specimen to displace in multiple directions.

19 Claims, 10 Drawing Sheets

APPARATUS FOR INTERFACING WITH A TEST SPECIMEN

FIELD

The current disclosure is generally directed at specimen testing and more specifically at an apparatus for interfacing with a test specimen.

BACKGROUND

Situations exist where it desirable to induce specified patterns of displacements, strains, loads or stresses in tissue engineering scaffolding materials, biological cells or substrates to which they are attached, specimens, objects or devices (targets). These include situations where mechanical properties are determined by applying particular loads or combinations of same in specific directions. Other situations include, but are not limited to, manufacturing processes, preconditioning of materials, use of stress or strain states to induce fiber alignment, crystallization in the material or to otherwise regulate, alter or transform its properties or structure at the bulk, meso, micro or nano scale, and where such targets are used as a substrate for other materials.

When only a few attachment points are used, the strain pattern in the specimen can be quite different from the intended pattern (for example, a uniform strain field). Using many attachment points can be time consuming, and precise location of those points can be crucial to achieving the desired strain fields. Mechanisms having many levers or similar machinery can provide multiple attachment points that move in synchrony, but they tend to be expensive and complex to design and fabricate.

SUMMARY

It is the aspect of the disclosure to provide a system and apparatus for interfacing with a, target or test specimen. In one embodiment, the apparatus is a mechanical interface located between a set of actuators and the target or test specimen. One advantage of the interface is that the number or complexity of the set of actuators needed to produce loads, displacements, stresses or strains of acceptable quality in the test specimen may be reduced with respect to current systems. Another advantage is that an increased number of loads, displacements, stresses or strain patterns than currently available may be possible with the interface disclosed within using fewer components. Another advantage of the disclosure is an apparatus which may facilitate transfer of the load or displacements from the actuator to the target, or a combination thereof.

In one embodiment, the interface is a deformable body that attaches to one or more actuators or fixed points. Through mechanical interaction of the interface with the test specimen, multiple displacements, strains, stresses or loads may be applied to the test specimen through a single actuator. Although multiple actuators may be used, one advantage of the current disclosure is that multiple displacements may also be provided to the target through the use of a single actuator.

In one embodiment, the attachment, connection and carrier elements are integrated into a single system, thereby facilitating handling, alignment and attachment, and improving functional repeatability and ease of use. A large number of specimen attachment points or regions may be used, and the target may be cast against the interface or may be monolithic with it.

In contrast to known systems, in one embodiment, the disclosure is directed at an apparatus having many attachment points that may be controlled with actuators or positioned easily.

BRIEF DESCRIPTION OF THE DRAWINGS

The invention will now be described in detail, with reference to the accompanying drawings of preferred and exemplary embodiments, in which.

DETAILED DESCRIPTION

The disclosure is directed at a system, apparatus and method for introducing a load, displacement, strain, stress or the like to a target or test specimen. Examples of test specimens include, but at not limited to, polymers, composites, biomaterials, cells or substrates to which they are attached, including tissue scaffolds, tissue constructs and gels. One advantage of the current disclosure is a system which is more cost effective than current systems as less actuators may be required to actuate the same number of contact points. In one embodiment, the system includes a deformable body which is connected to the specimen at at least two contact points. The deformable body may then distort in such a fashion that a prescribed pattern of stress, strain, loads or displacements may be applied to the specimen. In the following description, for simplicity, the word displacement will be used to represent a strain, stress, displacement or load being applied to the test specimen by a set of actuators via the interface.

Figure 1:
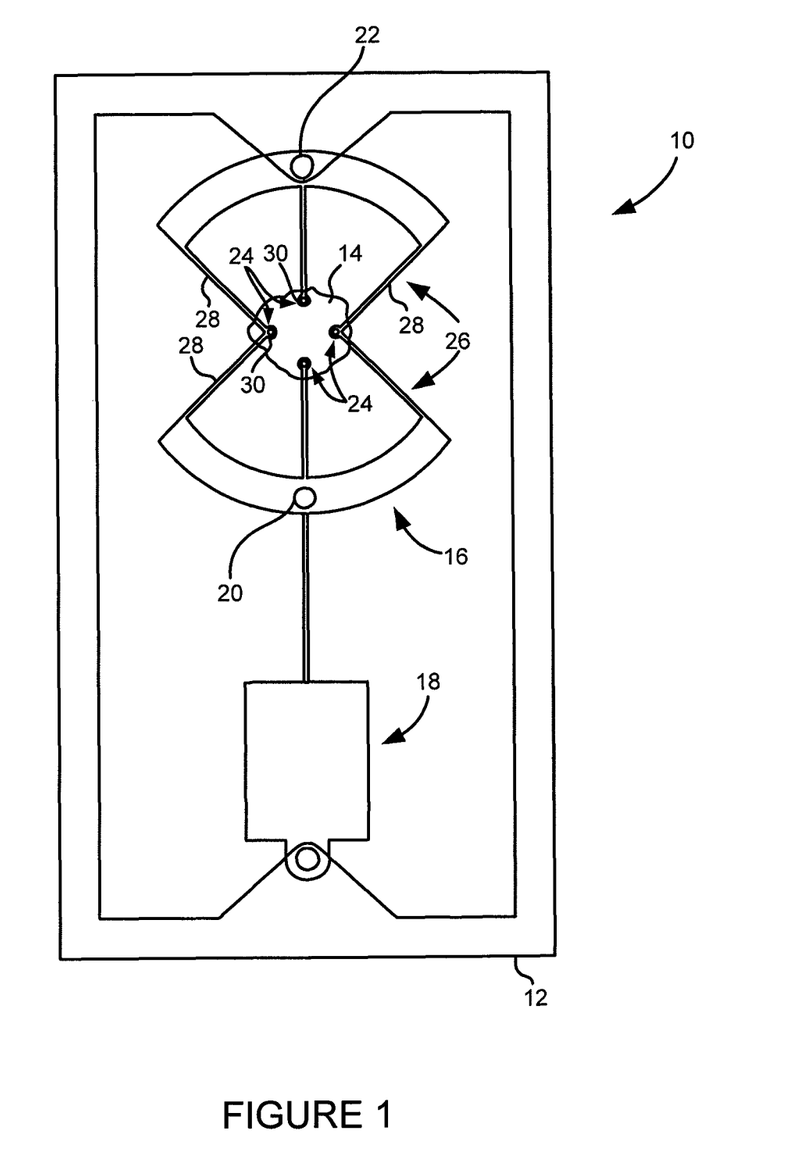
FIG. 1 is a schematic illustration of system for applying a displacement to a test specimen.

Turning to FIG. 1, a first embodiment of a system for introducing a displacement to a test specimen is shown. As discussed above, the system 10 includes a frame 12 or a housing and may be used for the application of one or more specified displacements to the test specimen 14, or target material object. Examples of test specimens are disclosed above. The system 10 includes an interface 16, which in the current embodiment, is attached to an actuator 18 via an actuator connection point 20 and may also attach to the frame at at least one location, or fixed connection point 22. In alternative embodiments, the interface 16 may connect with more than one actuator 18 or to the frame at more than one fixed connection point 22.

In one embodiment, the interface 16 comprises one or more flexible or deformable bodies, which may be interconnected to each other. In the embodiment of FIG. 1, the interface 16 includes a single deformable body which is connected to the specimen 14 at multiple target, or specimen contact or attachment points 24 via a set of connecting members 26. In the current embodiment, there are four specimen attachment points 24 although, as will be described below, the number of specimen attachment points 24 may be varied and dependent on the design of the interface 16. The connecting members 26 are preferably made from and include an arm portion 28 and a connector portion 30.

Figure 2A:
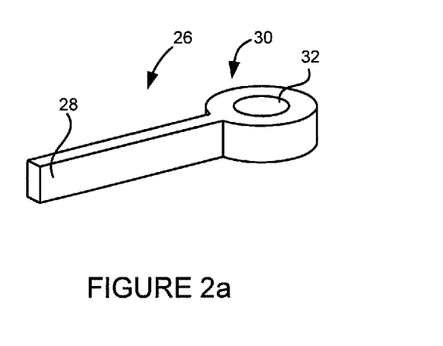
FIGS. 2a to 2f are schematic diagrams of connecting members of the system of FIG. 1.
Figure 2B:
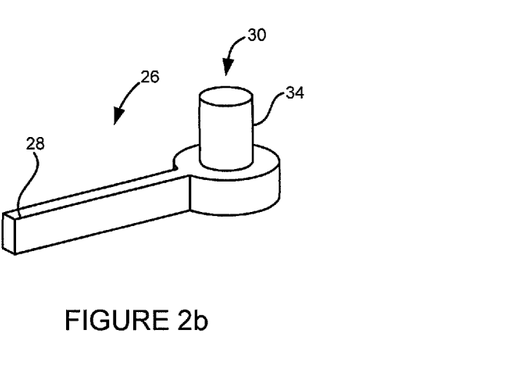
Figure 2C:
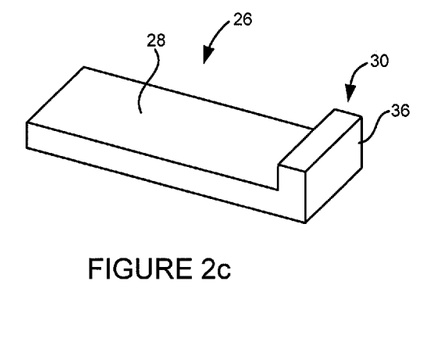
Figure 2D:
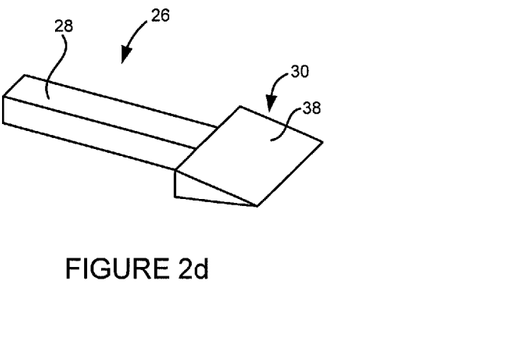
Figure 2E:
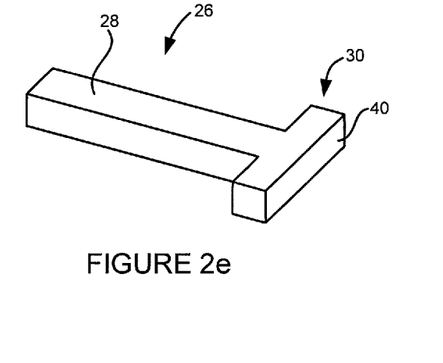
Figure 2F:
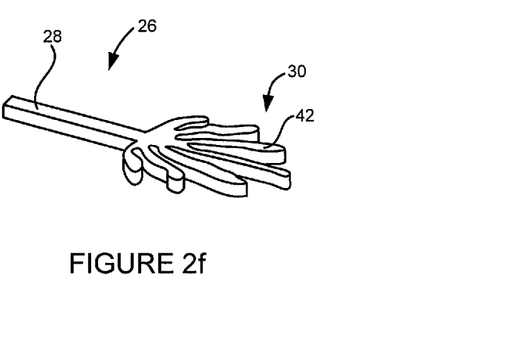

Turning to FIGS. 2a to 2f, examples of connecting members 26 are shown. In FIG. 2a, the connector portion 30 of the connecting member 26 is a ring 32. In the remaining FIGS. of 2b to 2f, the connector portion 30 is a pin 34 (FIG. 2b), a boss 36 (FIG. 2c), a tab 38 (FIG. 2d), an interlocking shape 40 (FIG. 2e) or a feathered feature 42 (FIG. 2f). The connection portion 30 may be any other mechanical features which enables attachment of the connecting member 26 to the test specimen 14. With respect to the tab of FIG. 2d and any of the other connecting members 26, adhesive may be used to further solidify the connection or contact between the connecting member 26 and the specimen 14. In other embodiments, the connector portion 30 may form part of the actuator 18, the interface 16 or the test specimen 14.

With respect to the interface 16, the interface 16 may be constructed or formed from a metal, polymer, biomaterial, semiconductor, glass, composite or other material which is elastic, plastic or visco-elastic in behavior, or in other words, deformable. The interface 16 may be designed to interact mechanically with the specimen 14 or the actuator 18, or actuators if multiple ones are necessary. For example, if the stiffness of the interface 16 is similar to that of the test specimen 14, the interface 16 and the test specimen 14 may interact mechanically, and the motions of the specimen attachment points 24 would be affected by the mechanical properties of the specimen 14. If this is the case, the specimen 14 and the interface 16 may be seen as a single piece and treated as such.

Figure 3A:
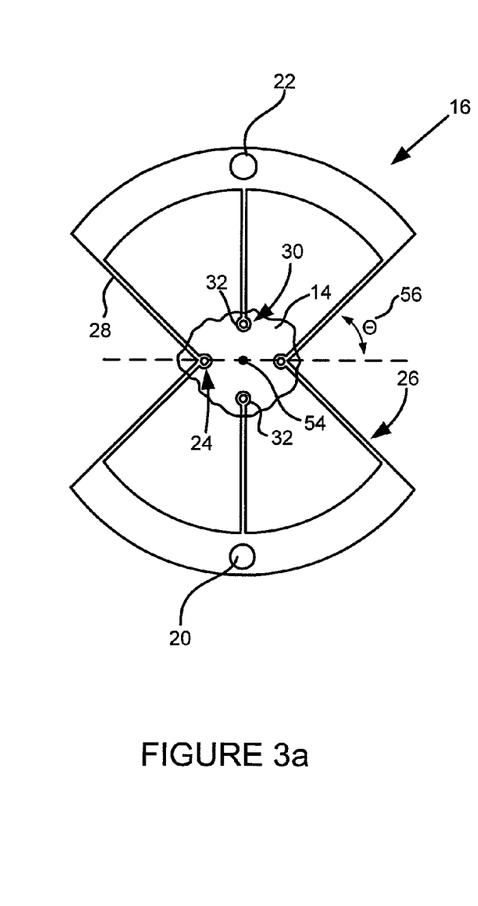
FIG. 3a is a schematic diagram of one embodiment of an interface connected with the test specimen.
Figure 3B:
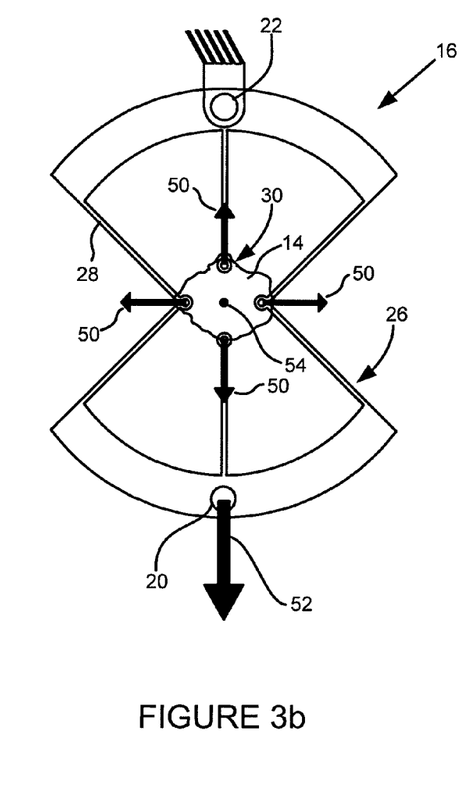
FIG. 3b is a schematic diagram of the embodiment of FIG. 3a with displacement vectors.

FIGS. 3a and 3b illustrate one embodiment of the interface, however, different embodiments of the interface 16 may be designed. In the embodiment of FIGS. 3a and 3b, the specimen attachment points 24 of target specimen 14 may be displaced, strained or stressed in multiple directions by a single actuator 18. As more clearly shown in FIG. 3a, the interface 16 includes a set of four connector members 26 having rings 32 as their connector portion 30. The rings 32 may be connected to the test specimen 14 via pins which are inserted into the rings 32 and then pierced through the specimen 14. The selection of the characteristics of the pins, such as size, shape, diameter or length will be such that when the displacement is applied to the test specimen 14, the specimen will generally not rip, tear or be destroyed by the actuated motion.

In one variant, this embodiment is designed to produce a strain as large as 10% where, for purposes of this statement, strain is defined as the change in length of a line between any two opposing specimen attachment points 24 divided by the original length between them. While it is preferred that the displacement of each of the specimen attachment points 24 are equal in magnitude and the directions of the displacements are different from each other, other embodiments may be possible where the displacements are different in magnitude. FIG. 3b illustrates a series of specimen displacement vectors 50 of the specimen attachment points 24 which may be experienced in the current embodiment when an actuated motion is produced by the actuator. The specimen displacement vectors 50 are in relationship with the displacement produced by the actuator 18 (connected to the actuator connection point 20), and is represented by actuator displacement vector 52. The displacement vectors 50 are measured relative to the centroid, or central portion 54 of the specimen 14.

In the current embodiment, the specimen displacement vectors 50 are uniform in the sense that all vectors 50 have the same magnitude. In a one actuator and one fixed point embodiment, this may be controlled by an angle parameter (Θ) 56 between the connecting members 26 and an imaginary axis normal to a line between the actuator connection point 20 and the fixed connection point 22. This is a first order approximation of the deformed connecting members that performs well over the 10% strain region of interest. In this embodiment, equal displacements are produced in the various attachment points when the angle 56 is 45 degrees.

In general, the angle 56 may can be approximately related to a ratio of the magnitude of the desired displacement parallel to the displacement produced by the actuator to the magnitude of the displacement normal to the displacement produced by the actuator. This may be more simply defined by the equation Θ=Arctan(ratio) with both magnitudes taken with respect to the imaginary axis.

In developing other interface embodiments, a finite element analysis or similar analytic study of the deformation of the interface or an experimental study of a physical prototype may be used to improve the actual ratios of the displacement vectors and motion patterns. If the specimen were sufficiently stiff compared to the interface 16, such techniques may be necessary to obtain desired motions at the specimen attachment points 24 or desired patterns of motion within the target.

Figure 4A:
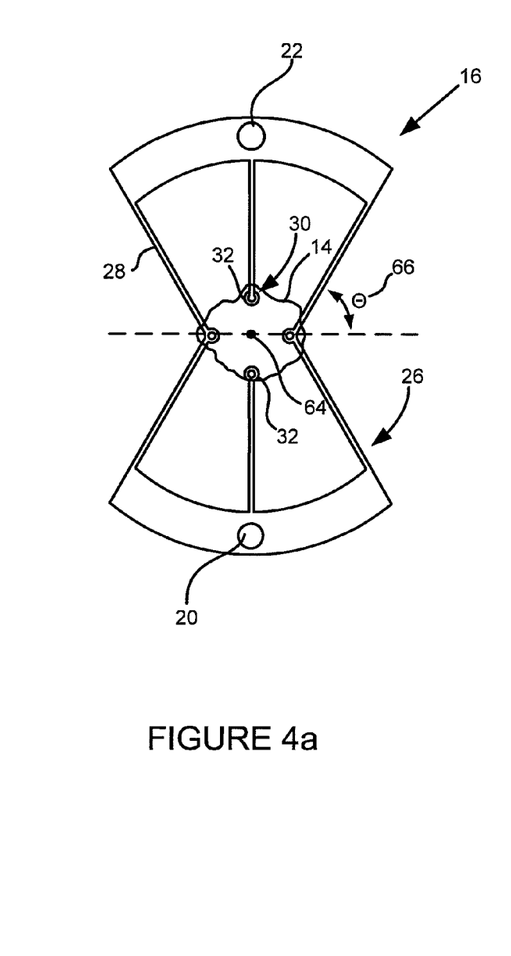
FIG. 4a is a schematic diagram of another embodiment of an interface connected with a test specimen.
Figure 4B:
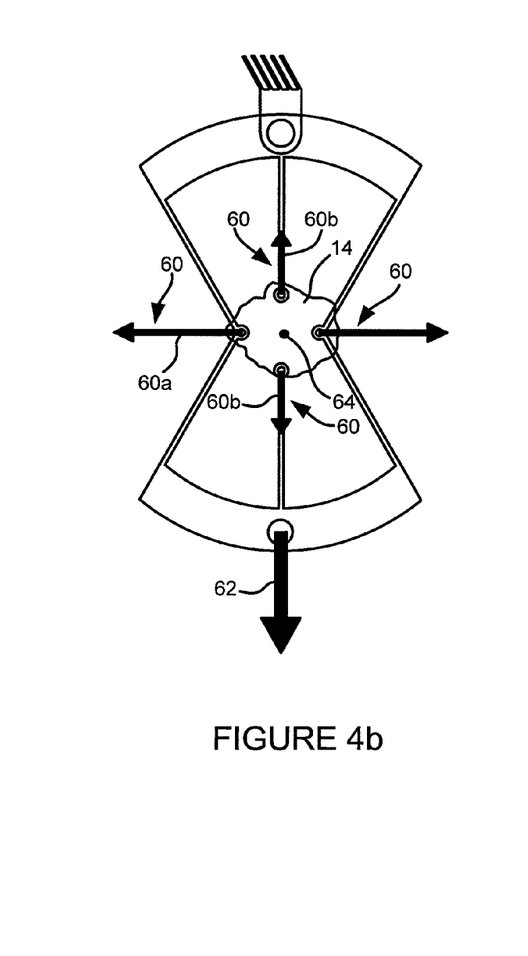
FIG. 4b is a schematic diagram of the embodiment of FIG. 4a with displacement vectors.

FIGS. 4a and 4b are directed at another embodiment of an interface for use with the system of FIG. 1. As with the embodiment of FIGS. 3a and 3b, a single motion produced by the actuator 18 (connected to the actuator connection point 20) causes the specimen attachment points 24 of the test specimen 14 to move in multiple directions due to the deformable interface 16. As with the previous embodiment, this interface 16 may be designed to produce strains as large as 10% in the specimen, however the displacements at the specimen attachment points 24 are not equal in magnitude. As shown in FIG. 4b which includes specimen displacement vectors 60 of the target attachments and an actuator displacement vector 62 created by the single actuator 18. Both the target and actuator displacement vectors are defined relative to the centroid 64 of the test specimen 14. With respect to the specimen displacement vectors, in the current embodiment, they may be seen as specimen displacement vectors parallel to produced actuator motion 60b and specimen displacement vectors normal to produced actuator motion 60a.

The geometry of the interface 16 may be designed such that the target displacement vectors are not equal, but rather, such that specimen vectors 60a have twice the magnitude of specimen vectors 60b. As with the embodiment above, the ratio of the magnitude of the displacements is controlled by the angle parameter (Θ) 66 between the connecting members 26 and the imaginary axis. In this embodiment angle (Θ) 66 is approximately 63.4 degrees as determined using the equation Θ=Arctan(ratio) and the ratio of the displacements normal to the actuator axis to those parallel to it is two. By using this equation, the angle 66 may be selected such that this ratio may be controlled. In the current embodiment, individual interfaces 16 are produced with different (Θ) values, however, it may be designed in the future where the angle (Θ) of the interface may be continually changed when desired by a user.

Figure 5A:
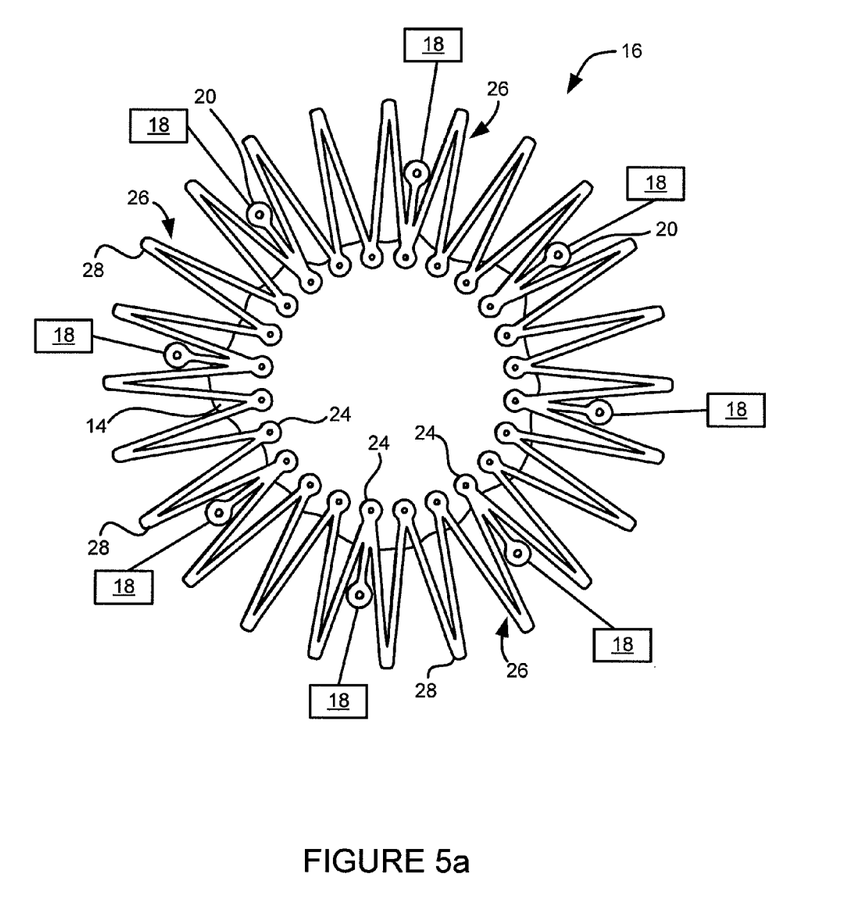
FIG. 5a is a schematic diagram of another interface for use with the system of FIG. 1.

Turning to FIG. 5a, an example of another embodiment of an interface is shown. In this embodiment, the interface may perform an interpolation function. In this embodiment, the interface 16 includes a set of actuators 18 which are connected to the interface 16 via a set of actuator connection points 20. As can be seen, the set of actuator connection points 20 are connected with a set of specimen attachment points 24 whereby displacement of at least one of the connection points 20 causes a displacement on the specimen via the specimen attachment points 24. Although, in a preferred embodiment, the displacement produced by the actuators 18 is co-ordinated, each of the actuators 18 may be individually operated. As with the interfaces 16 described above, the interface is manufactured from a deformable material whereby the connecting members 26 may be controlled via the displacement of at least one of the actuators.

Figure 5B:
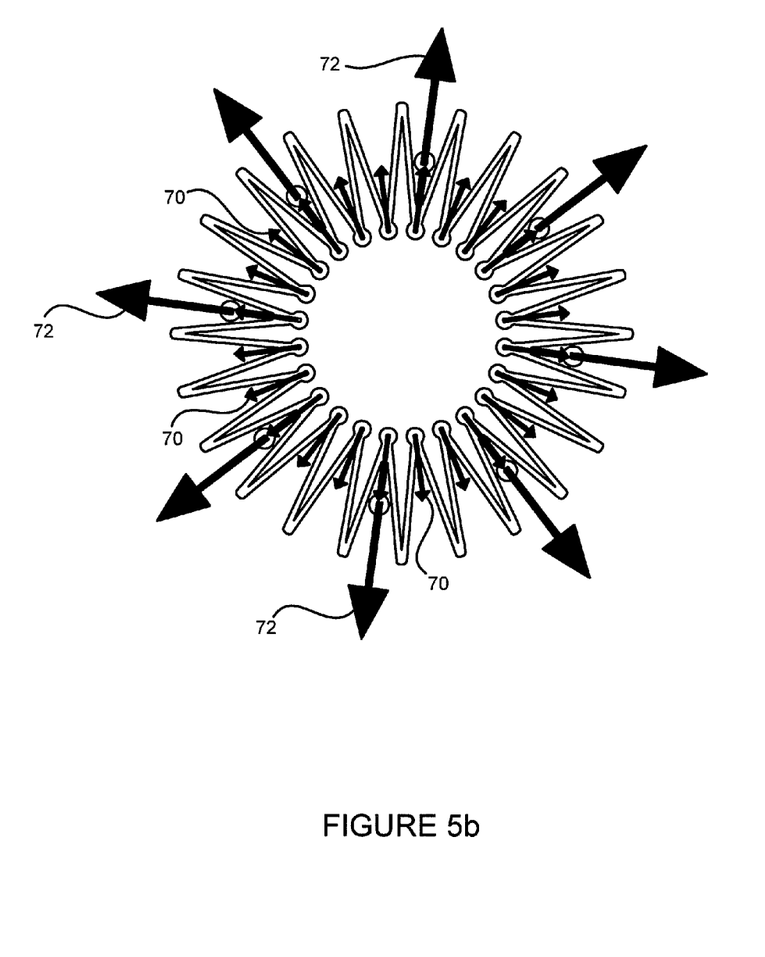
FIG. 5b is a schematic diagram of the embodiment of FIG. 5a with displacement vectors.

FIG. 5b illustrates a more detailed view of the interface 16 of FIG. 5a. In this embodiment, displacements of the specimen attachment points 24 are initiated by multiple actuators 18 and actuator connection points 20 with the interface 16 providing a form of mechanical interpolation of the displacement of the actuators 18. In this embodiment, the interface 16 may not be attached to the housing such that there are no fixed attachment points 22. Specimen displacement vectors 70 of the specimen attachments points 24 and the actuator displacement vectors 72 created by the multiple actuators 12 as shown and in this embodiment the specimen displacement vectors are equal in magnitude and radial in direction.

Figure 6:
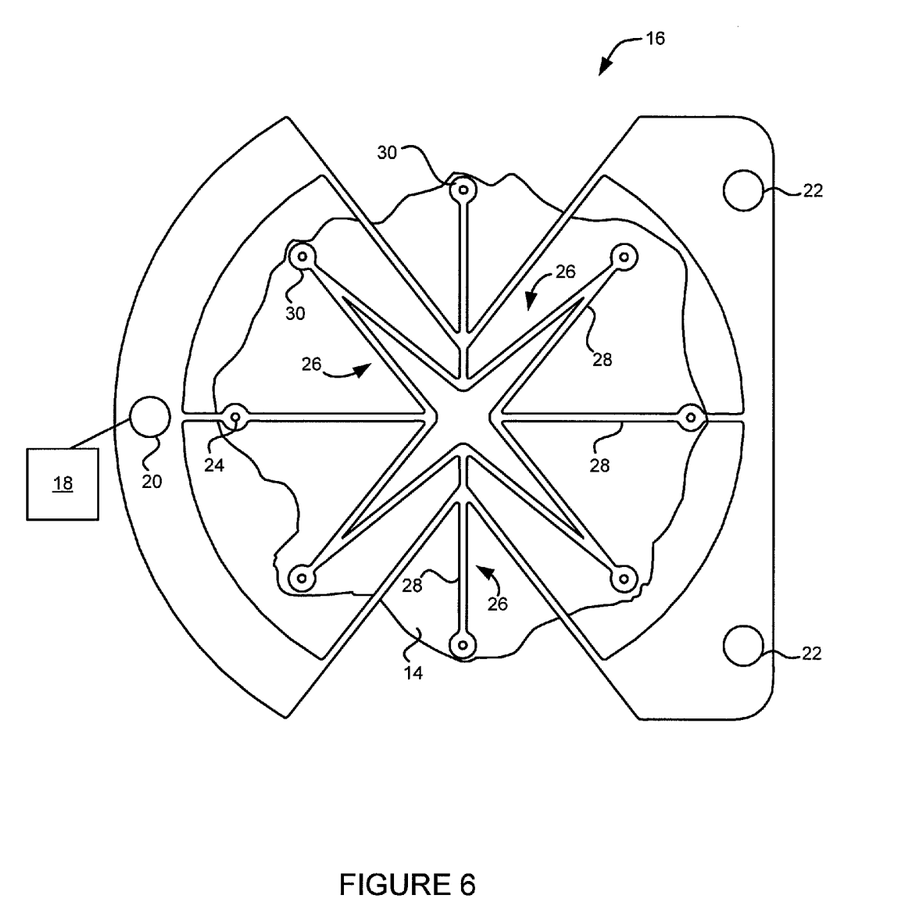
FIG. 6 is a schematic diagram of yet another interface for use with the system of FIG. 1.

Turning to FIG. 6, yet another embodiment of an interface for use with the system 10 is shown. In this embodiment, the interface 16 may include one actuator connection point 20 for connecting with the actuator 18 and two fixed connection points 22 where the interface 16 is connected to a housing. The connecting members 26 include rings 32 as the connector portions and are in contact with the specimen 14 such as via needles, or pins or the like. In operation, movement of the actuator connection point 20 via the actuator 18 causes the specimen to be displaced at multiple locations, seen as the specimen attachment points 24.

Figure 7:
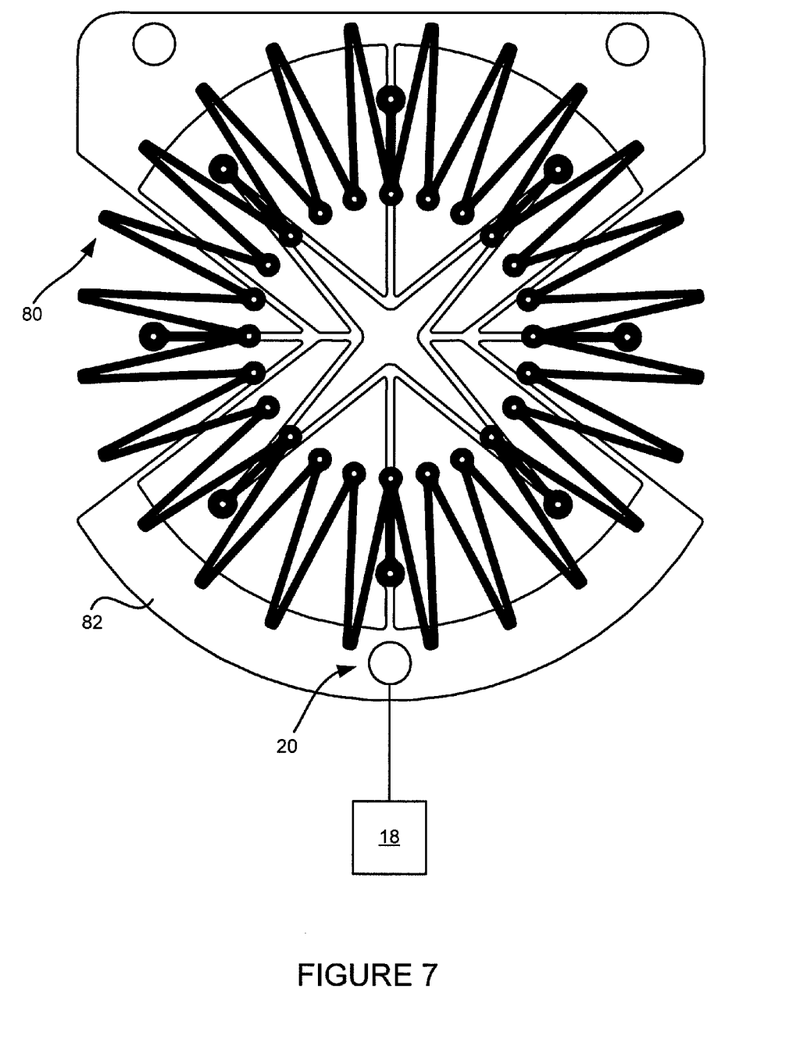
FIG. 7 is a schematic diagram of yet a further interface for use with the system of FIG. 1.

Turning to FIG. 7, yet a further embodiment of an interface is shown. In this embodiment, multiple interfaces may be combined to form a single or composite interface such as by the combination or stacking of the interfaces of FIGS. 5 and 6. For clarity, the interface of FIG. 5 will be represented by the reference number 80 and the interface of FIG. 6 will be represented by the reference number 82. In this embodiment, the actuator connection point 20 of interface 82 is connected to the actuator 18 while the other fixed attachment points 22 are connected to fixed locations, such as the housing of the system 10 so that they are stationary when the actuator produces its displacement. Although not clearly shown, the specimen attachment points 24 of interface 82 may be connected to the actuator connection points 20 of interface 80. The specimen attachment points 24 of interface 80 are connected to the specimen. In operation, a single actuator may be able to provide multiple displacements to the specimen thereby providing a lower cost option than other systems. Movement by the actuator causes the connecting members of interface 82 to displace, thereby moving the connector members of interface 80 thereby causing the specimen attachment points interface 80 to displace the specimen in multiple directions.

Figure 8:
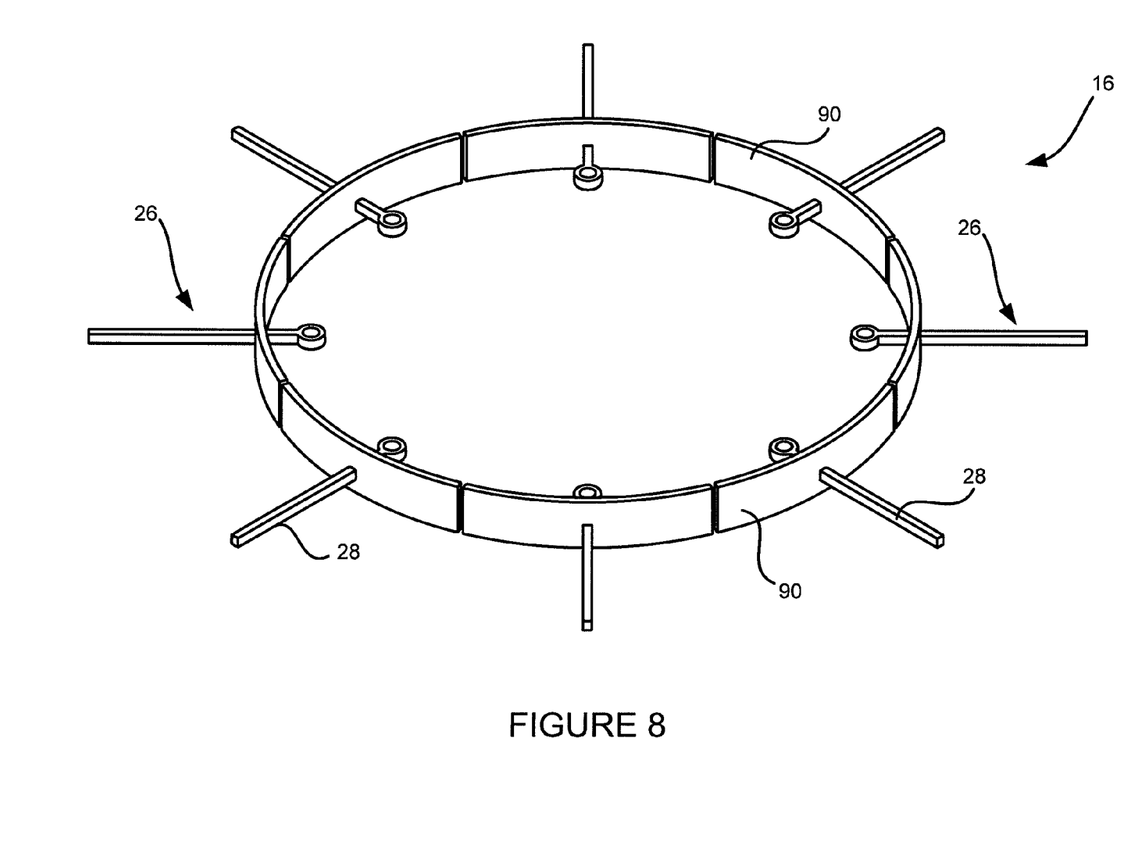
FIG. 8 is a schematic diagram of yet a further interface for use with the system of FIG. 1.

Turning to FIG. 8, another embodiment of an interface for use with the system 16 is shown. In this embodiment, the interface 16 includes an enclosure or mould with a plurality of walls 90, each of the walls including a connecting member 26 located therein. The walls 90 may be used to form a mould against which the test specimen may be cast. In other embodiments, the connecting members 26 and the walls do not need to be in a one to one relationship. Although not shown, the interface 16 includes an actuator connection point 20 for connecting the interface with an actuator.

The walls 90 form an enclosed space whereby a liquid test specimen may be poured so that it may be solidified grown, or gel around the connector portions 30 of the connecting means.

Figure 9:
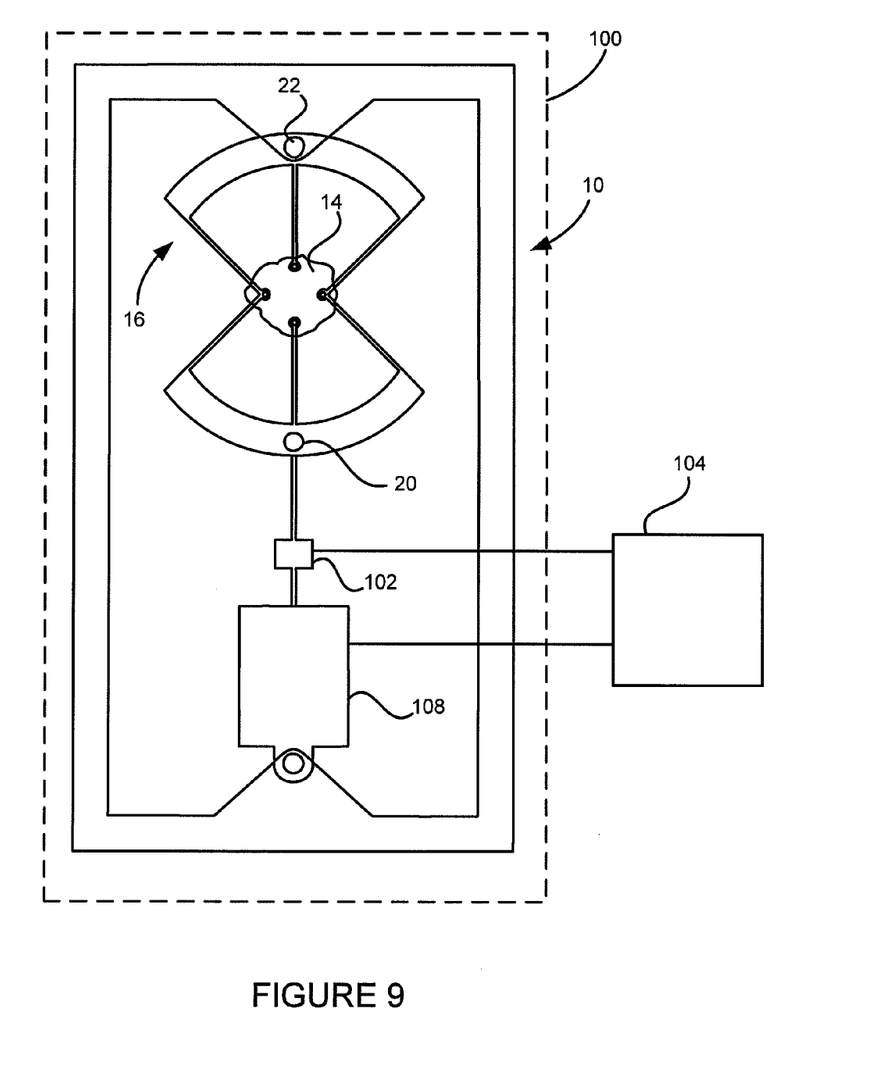
FIG. 9 is a schematic diagram of a further embodiment of a system for applying a displacement to a test specimen.

FIG. 9 is directed at an embodiment of the system integrated within an apparatus. As shown, the system 10 may be housed within an incubator 100 which is used to control the surrounding environment, including its temperature, humidity if non-aqueous, and chemistry including pH. A load cell 102 may be located between the actuator connection point 20 and the actuator 18 with both the load cell and the actuator connected to a central processing unit (CPU) 104, or computer which may transmit or receive signals to and from the load cell and actuator. For instance, the CPU 104 may receive load cell measurements indicating the amount of displacement or load which is being delivered to the specimen 14 or to transmit a signal to the actuator 18 indicating how much displacement is required.

In alternative embodiments, the interface may be engineered to facilitate the production of a desired pattern of displacement in the specimen. These patterns may be characterized by uniformity, gradients, multiple functional zones, anisotropy or periodicity. By suitable design, it may be possible to obtain a desired pattern of displacement vectors in directions other than the actuator direction vector, thus using fewer actuators 18 or actuators with less complex motions. It may also be possible to more closely approximate a desired condition, such as uniform strain, with a fixed number of actuators than if an interface 16 is not used.

Some applications for the system or interface include, but are not limited to, materials preconditioning or testing and manufacturing processes, and materials that include polymers, tissues, biomaterials, composites and gels.

In yet another alternative embodiment, the specimen attachment points may move in a path that is not a straight line, whether the actuator motion is or is not, and that increments in the displacement of specimen attachment points associated with increments in actuator motion need not be in proportion to each other. Nonlinear, smart, or otherwise complex materials may be used in fabrication of the interface so as to produce complex attachment point motions or motions that respond to target response, or so that fewer or less precise actuators could be used to produce a desired displacement pattern in the target.

Although in most embodiments, the interface is shown as a planar interface 16, three-dimensional interfaces are also contemplated which may produce displacements of the specimen that are not co-planar.

In another embodiment, the connecting members may not include arm portions and may simply be blob-like with connection portions which may attach to the test specimen.

In the preceding description, for purposes of explanation, numerous details are set forth in order to provide a thorough understanding of the embodiments; however the specific details are not necessarily required. In other instances, well-known electrical structures and circuits are shown in block diagram form in order not to obscure the understanding. For example, specific details are not provided as to whether the embodiments described herein are implemented as a software routine, hardware circuit, firmware, or a combination thereof.

The above-described embodiments are intended to be examples only. Alterations, modifications and variations can be effected to the particular embodiments by those of skill in the art without departing from the scope, which is defined solely by the claims appended hereto.

The invention claimed is:

1. An apparatus for interfacing with a test specimen comprising:
   a deformable body having a set of connecting members and at least one actuator connection point;
   wherein the connecting members are attached to the test specimen at specimen attachment points and whereby a displacement applied to the at least one actuator connection point causes the test specimen to displace via the set of connecting members in at least one controlled direction that is different from the displacement applied to the at least one actuator connection point.

2. The apparatus of claim 1 wherein the connecting members are attached to the test specimen in spaced-apart locations.

3. The apparatus of claim 1 wherein the deformable body comprises at least one fixed attachment point for attaching the interface to an apparatus housing.

4. The apparatus of claim 3, wherein the number of specimen attachment points is greater than the sum of the fixed attachments and actuator attachments.

5. The apparatus of claim 4, where there is no fixed stationary attachment points, such that the number of specimen attachment points is always greater than the sum of the at least one fixed attachment point and the at least one actuator connection point.

6. The apparatus of claim 1, where a geometry of the connecting members is designed to displace the specimen attachment points in equal magnitude and radial directions.

7. The apparatus of claim 1, where a geometry of the connecting members is designed to displace the specimen attachment points by differing magnitudes or nonlinear directions.

8. The apparatus of claim 1 wherein the connecting members comprise:
   a connector arm; and
   a connection portion.

9. The apparatus of claim 8 wherein the connection portion is selected from the group consisting of: a ring, a pin, a boss, a tab, an interlocking shape and a feathered feature.

10. The apparatus of claim 1 further comprising a second deformable body, the second deformable body having a set of second body connecting members and at least one second body actuator connection point.

11. The apparatus of claim 10 wherein the specimen attachment points of the deformable body are connected to the at least one second body actuator connector point and the set of second body connecting members are connected to the specimen;
   whereby displacement applied to the at least one actuator connection point of the deformable body causes the test specimen to displace via the set of second body connecting members.

12. The apparatus of claim 1 wherein the deformable body is manufactured from a material which is elastic, plastic or visco-elastic in behavior.

13. The apparatus of claim 12 wherein the material is selected from the group consisting of metal, polymer, biomaterial, semiconductor, glass and a composite material.

14. The apparatus of claim 1 further comprising an actuator connected to each of the at least one actuator connection point.

15. The apparatus of claim 1 further comprising an enclosure for containing the test specimen.

16. The apparatus of claim 15 wherein the enclosure comprises a set of walls.

17. The apparatus of claim 1 further comprising apparatus to attach a membrane, scaffold, carrier or tissue with embedded or adhered or attached or otherwise supported cells to apply mechanical deformation.

18. The apparatus of claim 1 wherein the predetermined direction is non-perpendicular and non-parallel from the displacement applied to the at least one actuator connection point.

19. The apparatus of claim 1 wherein the displacement applied to the at least one actuator connection point purposefully causes the test specimen to displace in the predetermined direction.

* * * * *